United States Patent
Duclos

(10) Patent No.: US 11,883,529 B2
(45) Date of Patent: Jan. 30, 2024

(54) METHODS OF ADMINISTERING ANTI-EPILEPSY AGENTS AND TRANSPORT INHIBITORS TO A SUBJECT

(71) Applicant: Medtronic, Inc., Minneapolis, MN (US)

(72) Inventor: Brian A. Duclos, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 225 days.

(21) Appl. No.: 17/394,588

(22) Filed: Aug. 5, 2021

(65) Prior Publication Data

US 2022/0062171 A1 Mar. 3, 2022

Related U.S. Application Data

(60) Provisional application No. 63/071,617, filed on Aug. 28, 2020.

(51) Int. Cl.
*A61K 9/00* (2006.01)
*A61K 9/08* (2006.01)
*A61K 31/195* (2006.01)

(52) U.S. Cl.
CPC .............. *A61K 9/0085* (2013.01); *A61K 9/08* (2013.01); *A61K 31/195* (2013.01)

(58) Field of Classification Search
CPC ................................ A61K 9/0085; A61K 9/08
See application file for complete search history.

(56) References Cited

U.S. PATENT DOCUMENTS

| 4,692,147 A | 9/1987 | Duggan | |
|---|---|---|---|
| 2005/0090548 A1* | 4/2005 | Hildebrand | A61K 31/195 514/561 |
| 2010/0048538 A1* | 2/2010 | Soares Da Silva | A61P 25/02 514/217 |
| 2019/0151239 A1* | 5/2019 | Abrams | A61K 45/06 |

OTHER PUBLICATIONS

Cook et al. (EClinicaMedicine 22 (2020) 10326) Published May 2020.).*

* cited by examiner

*Primary Examiner* — Shirley V Gembeh
(74) *Attorney, Agent, or Firm* — Mueting Raasch Group

(57) ABSTRACT

Broad cerebrospinal fluid (CSF) distribution of an agent is achievable by delivering the agent in a liquid formulation to the CSF at flow rates less than 500 microliters per hour, such as between about 2 microliters per hour and about 100 microliters per hour.

20 Claims, 3 Drawing Sheets

METHODS OF ADMINISTERING ANTI-EPILEPSY AGENTS AND TRANSPORT INHIBITORS TO A SUBJECT

RELATED APPLICATIONS

This application claims the benefit under 35 U.S.C. § 119 of U.S. Provisional Application Ser. No. 63/071,617, filed Aug. 28, 2020, which is incorporated herein by reference in its entirety.

FIELD

This disclosure relates to methods for delivering antiepileptic agents, such as therapeutic agents, to the cerebrospinal fluid-containing intrathecal space of a subject for affecting epilepsy.

BACKGROUND

Drug pumps and catheters can be utilized to deliver drugs directly to the cerebrospinal fluid (CSF) to treat conditions that effect the brain. Once that has been accomplished however, the blood brain barrier still functions to exclude foreign agents from the brain itself. One mechanism utilized to exclude such agents is via membrane-bound transport inhibitors. Disclosed methods provide solutions to the problem of the susceptibility of antiepileptic drugs to CSF transport inhibitors.

SUMMARY

In embodiments, a method for affecting epilepsy in a subject, the method comprising: administering a liquid formulation comprising an antiepileptic compound to an CSF-containing intrathecal space of the subject; and administering a liquid formulation comprising a multidrug resistance protein (MRP) inhibitor compound to an CSF-containing intrathecal space of the subject.

In embodiments, a method for affecting epilepsy in a subject, the method comprising: administering a liquid formulation comprising valproic acid to an CSF-containing intrathecal space of the subject; and administering a liquid formulation comprising a multidrug resistance protein (MRP) inhibitor compound to an CSF-containing intrathecal space of the subject.

Disclosed methods may provide higher efficacy of known drugs, use of known or unknown drugs, or combinations thereof. Additionally, or alternatively, disclosed methods may provide sufficient exposure via intrathecal delivery as opposed to relying on direct delivery through the brain.

One or more embodiments described herein present one or more advantages over other methods of treating epilepsy. These and other advantages will be evident to those of skill in the art upon reading the disclosure presented herein.

Figure 1:
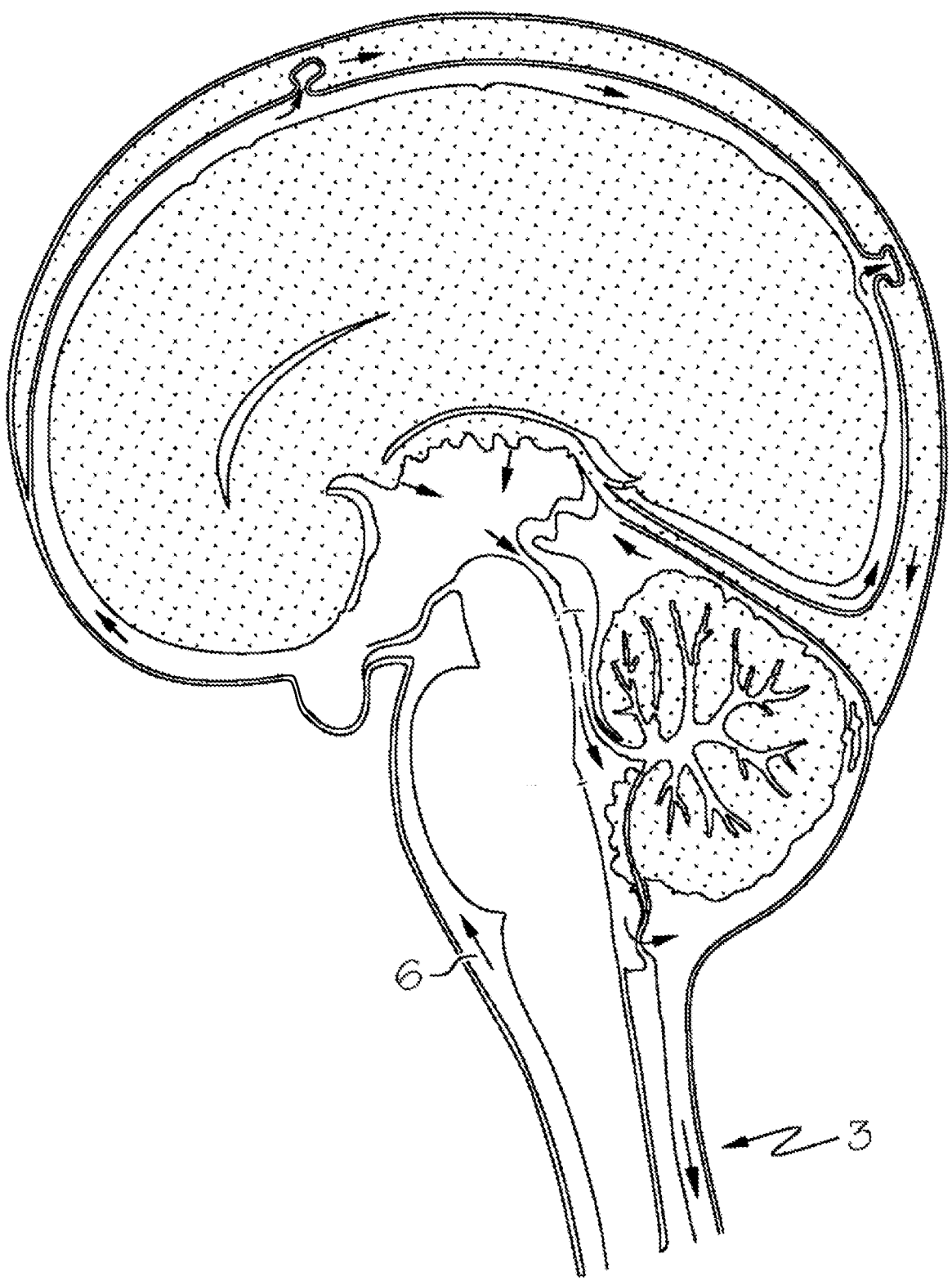
FIG. 1 is a schematic drawing of a section of a brain and portions of a spinal cord showing cerebrospinal fluid flow.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

The following description illustrates various embodiments. It is to be understood that other embodiments are contemplated and may be made without departing from the scope or spirit of the present invention. Thus, the following description is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

As used herein, the singular forms "a", "an", and "the" encompass embodiments having plural referents, unless the content clearly dictates otherwise.

As used herein, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

As used herein, the terms "treat" or the like means alleviating, slowing the progression, preventing, attenuating, or curing the treated disease.

As used herein, "disease", "disorder", "condition" or the like, as they relate to a subject's health, are used interchangeably and have meanings ascribed to each and all of such terms.

As used herein, "subject" means a mammal to which an agent is administered for the purposes of treatment or investigation. Mammals include mice, rats, cats, guinea pigs, hamsters, dogs, sheep, monkeys, chimpanzees, and humans.

Drug pumps and catheters can be utilized to deliver drugs directly to the cerebrospinal fluid (CSF) to treat conditions that effect the brain. Once that has been accomplished however, the blood brain barrier still functions to exclude foreign agents from the brain itself. One mechanism utilized to exclude such agents is via membrane-bound transport inhibitors. Disclosed methods provide solutions to the problem of the susceptibility of antiepileptic drugs to CSF transport inhibitors.

The present disclosure relates to administering an antiepileptic drug and a multidrug resistant protein (MRP) inhibitor compound to the CSF. The antiepileptic drug and the MRP inhibitor compound can be administered simultaneously or substantially simultaneously for the treatment of epilepsy. In some embodiments, the antiepileptic drug and the MRP inhibitor compound can be present in a single liquid formulation, and in some embodiments in two liquid formulations. In some embodiments, the antiepileptic drug and the MRP inhibitor compound can be delivered from two liquid formulations but via a single catheter, for example. In some embodiments, the antiepileptic drug and the MRP inhibitor compound can be present in a single liquid formulation and can be delivered from the single liquid formulation via a single catheter.

Useful antiepileptic drugs can include, for example carbamazepine, clobazam, clonazepam, eslicarbazepine acetate, felbamate, gabapentin, lacosamide, lamotrigine, levetiracetam, oxcarbazepine, phenobarbital, phenytoin, pregabalin, primidone, rufinamide, stiripentol, tiagabine, topiramate, valproic acid, vigabatrin, and zonisamide. In some embodiments, the antiepileptic drug can include, for example valproic acid.

Useful MRP inhibitor compounds can include, for example probenecid, pyrimethamine, reversan, ceefourin 1, MK 571, or combinations thereof. In some embodiments, the MRP inhibitor compound can include probenecid, for example.

According to various embodiments, administering may include delivering directly to cerebrospinal fluid 6 of a subject. Referring to FIG. 1, cerebrospinal fluid (CSF) 6 exits the foramen of Magendie and Luschka to flow around the brainstem and cerebellum. The arrows within the subarachnoid space 3 in FIG. 2 indicate cerebrospinal fluid 6 flow. The subarachnoid space 3 is a compartment within the central nervous system that contains cerebrospinal fluid 6. The cerebrospinal fluid 6 is produced in the ventricular system of the brain and communicates freely with the subarachnoid space 3 via the foramen of Magendie and Luschka. A liquid formulation including a molecule of interest may be delivered to cerebrospinal fluid 6 of a subject anywhere that the cerebrospinal fluid 6 is accessible. For example, the composition may be administered intrathecally (e.g., at a lumbar, sacral, thoracic or cervical level or into the cisterna magna).

The compound(s), drug(s) or the likes may be any known or future developed small molecule or biologic therapeutic agent. Examples of biologic therapeutic agents that may be employed in accordance with the teachings presented herein include antibodies or fragments thereof; inhibitory RNA molecules such as antisense RNA, microRNA (miRNA), small interfering RNA (siRNA), or the like; DNA; polypeptides; proteins; viruses, vectors or the like. The molecules may be used for therapeutic, diagnostic or investigatory purposes.

Generally, the molecules will be formulated into a liquid formulation suitable for delivery to the CSF. The formulation may include the molecule and a variety of other pharmaceutically acceptable components. See Remington's Pharmaceutical Science (15th ed., Mack Publishing Company, Easton, Pa. (1980)). The preferred form may depend on the intended application. The formulations may also include, depending on the formulation desired, pharmaceutically-acceptable, non-toxic carriers or diluents, which are defined as vehicles commonly used to formulate pharmaceutical compositions for animal or human administration. In most cases, the diluent is selected so as not to adversely affect the activity of the molecule of interest. Examples of such diluents are distilled water, physiological phosphate-buffered saline, artificial cerebrospinal fluid, citrate buffered saline, Ringer's solutions, dextrose solution, and Hank's solution.

Typically the liquid formulations are formed as injectable compositions. Injectable compositions include solutions, suspensions, dispersions, or the like. Injectable solutions, suspensions, dispersions, or the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Proper fluidity of solutions, suspensions or dispersions may be maintained, for example, by the formation of liposomes, by the maintenance of the desired particle size, in the case of dispersion, or by the use of nontoxic surfactants.

The prevention of microorganisms can be accomplished by heat sterilization or filter sterilization, whichever is compatible with the molecule and formulation being used. Isotonic agents such as sugars, buffers, or sodium chloride may be included. Solubility enhancers may be added.

In various embodiments, the final formulation is adjusted to have a pH between about 4 and about 9, between about 5 and about 7, between about 5.5 and about 6.5, or about 6. The pH of the composition may be adjusted with a pharmacologically acceptable acid, base or buffer. Hydrochloric acid is an example of a suitable acid, and sodium hydroxide is an example of a suitable base. The hydrochloric acid or sodium hydroxide may be in any suitable form, such as a 1N solution In various embodiments, a resultant fluid composition contains an amount of one or more molecules effective to treat a disease to allow meaningful study of a subject to which the composition is administered at a particular flow rate. The effective amount of the molecule to be administered will vary depending on the molecule itself and the disease to be treated. The amount may also vary depending on the subject to which it is administered and the location of administration (e.g., IT vs. ICV).

The liquid formulation containing the molecule of interest may be administered to the CSF in any suitable manner. In various embodiments, a system including an infusion device is used to deliver a liquid formulation containing a molecule of interest to subject. The system may further include a catheter operably coupled to the infusion device. The infusion device may include a drive mechanism or pump, such as a piston pump, peristaltic pump, positive pressure reservoir, or the like. Non-limiting examples of infusion devices include osmotic pumps, fixed-rate pumps, programmable pumps and the like. Each of the aforementioned pump systems contains a reservoir for housing the fluid composition and an outlet in fluid communication with the reservoir. The catheter may be operably coupled to the outlet. The catheter includes one or more delivery regions, through which the fluid may be delivered to one or more target regions of the subject. The infusion device may be implantable or may be placed outside the body via an externalized catheter outside the body, external to the subject. Alternatively an implanted port that is in direct communication with a CSF compartment via a catheter can be accessed on an intermittent basis and drug infused over the desired duration using an external pump delivering the drug at an appropriate rate as described herein.

The liquid formulation may be administered at any suitable rate to the subject's CSF to achieve broad distribution. In many embodiments, the composition is administered at a rate of less than 1 ml per hour, such as less than 500 microliters per hour. For example, the composition may be administered at a rate of less than 200 microliters per hour or between about 4 microliters per hour and 100 microliters per hour or between about 2 microliters per hour and 25 microliters per hour. It will be understood flow rates per hour may be converted to flow rates per minute, per second, per day, etc. using appropriate conversion factors and that, when properly converted, such flow rates are considered equivalent.

The infusion device may be configured to deliver the liquid formulation at these rates. By way of example, the infusion device may include electronics configured to control the rate at which the liquid formulation may be delivered from the reservoir to the outlet. In embodiments, the electronics are programmed with instructions that cause the liquid formulation to be delivered at the desired rates.

In any case, it may be desirable to limit the volume of therapeutic or diagnostic composition administered to the CSF of a subject to avoid adverse effects such as hydrocephalus or the like. For example, it may be desirable to limit the volume of therapeutic or diagnostic composition delivered per day to about 20% or less, about 15% or less, or about 10% or less, about 5% or less, or about 2% or less of the CSF volume of the subject to which the composition is delivered. By way of example, 10% of the CSF volume of a typical adult human is about 12.5 ml, and 5% of the CSF volume is about 6.25 ml.

To achieve a suitable flow rate to achieve broad distribution while conserving on the amount or volume delivered, a therapeutic or diagnostic composition may be delivered to a subject's CSF in pulsatile or episodic manner, as a controlled and programmed therapy rather than at a constant rate. For example, a therapeutic agent may be administered at a sufficiently high flow rate and duration to achieve desired distribution within the CNS, and then the flow rate would be reduced to a very low level for a prolonged period of time (days to weeks) to conserve drug and also maintain patency of the catheter. This pattern may be repeated on a chronic basis. It will be understood that nearly any other pulsatile dosage regimen may be employed and that the regimens discussed above are merely examples.

In some embodiments, between about 10 ml and 100 ml of a therapeutic or diagnostic composition is delivered to the CSF of a subject per month; e.g., about 20 ml/month or about 40 ml/month. A desired pulsatile delivery regimen may thus be calculated based on this desired volume. By way of example, if a flow rate of 2.4 ml per day is suitable to achieve desired CSF distribution and if it is desired to deliver 20 ml or less per month, the composition may be delivered at a rate of about 0.0017/min for one minute, every four minutes (or 15 times an hour). This would result in delivery of about 0.0255 ml/hour, 0.612 ml/day, or about 18.36 ml/month (assuming 30 days in a month). The rate, duration, and frequency of delivery may be modified as desired to achieve desired distribution and desired delivery volumes.

Preferably, the rate, duration, and frequency of delivery are determined such that an appropriate steady state concentration of therapeutic or diagnostic agent is achieved at desired CSF location. For example, if a therapeutic agent is delivered at an intrathecal location with the intention of having an effect at the brain, it would be desirable for steady state concentrations of the therapeutic agent in the CSF at, for example, the ventricles to be sufficiently high to be effective for treating a disease state. It will be understood that the CSF turnover rate and the tendency for the agent to diffuse out of the CSF may be accounted for in determining appropriate rates, durations, and frequencies of delivery, as well as concentrations of therapeutic agent.

Figure 2:
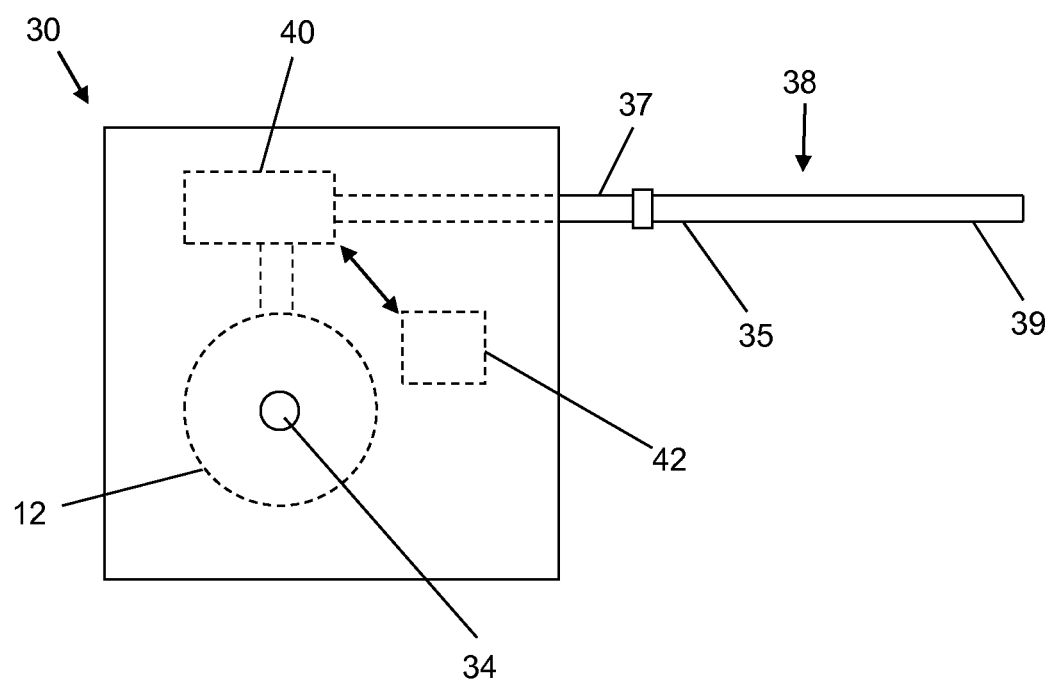
FIG. 2 is a schematic drawing of a side view of a representative infusion device system.

To assist in obtaining such dosage regimens, an infusion system may be employed. An example of an infusion system that may be employed is shown in FIG. 2. The system includes an infusion device 30 having a reservoir 12 for housing a fluid composition and a pump 40 operably coupled to the reservoir 12. The system further includes a catheter 38 having a proximal end 35 coupled to the infusion device 30 and a distal end 39 configured to be implanted in a target location of a subject. Between the proximal end 35 and distal end 39 or at the distal end 39, the catheter 38 has one or more delivery regions (not shown), such as openings, through which the fluid composition may be delivered. The infusion device 30 may have a port 34 into which a hypodermic needle can be inserted to inject the composition into the reservoir 12. The infusion device 30 may have a catheter port 37, to which the proximal end 35 of catheter 38 may be coupled. The catheter port 37 may be operably coupled to reservoir 12. The infusion device 30 may be operated to discharge a predetermined dosage of the pumped fluid into a target region of a subject at a predetermined rate. The infusion device 30 may contain a microprocessor 42 or similar electronics that can be programmed to control the amount and rate of fluid delivery. The programming may be accomplished with an external programmer/control unit via telemetry. With the use of a programmable infusion device 30, dosage regimens may be programmed and tailored for a particular subject. Additionally, different dosages can be programmed for different combinations of fluid compositions. Those skilled in the art will recognize that a programmable infusion device 30 allows for starting conservatively with lower doses and adjusting to a more aggressive dosing scheme, if warranted, based on safety and efficacy factors when used for therapeutic purposes.

Figure 3:
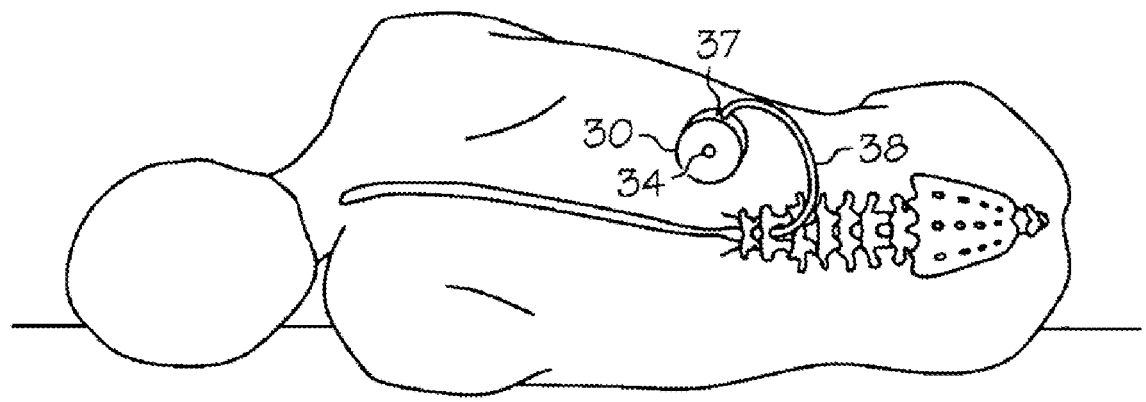
FIG. 3 is a schematic drawing of a view of an infusion device and associated catheter implanted in a patient.

FIG. 3 illustrates an example of an infusion system configured for intrathecal delivery of a composition containing a molecule of interest. As shown in FIG. 3, a system or device 30 may be implanted below the skin of a patient. Preferably the device 30 is implanted in a location where the implantation interferes as little as practicable with activity of the subject in which it is implanted. Device 30 may take the form of the like-numbered device shown in U.S. Pat. No. 4,692,147 (Duggan), assigned to Medtronic, Inc., Minneapolis, Minn., take the form of a SynchroMed II infusion device (Medtronic, Inc.), or take the form of any currently available or future developed infusion device. One suitable location for implanting the device 30 is subcutaneously in the lower abdomen. In various embodiments, catheter 38 is positioned so that the distal end 39 of catheter 38 is located in the subarachnoid space 3 of the spinal cord such that a delivery region (not shown) of catheter is also located within the subarachnoid space 3.

In many embodiments, a composition containing a molecule is administered intrathecally at a low flow rate to achieve distribution of the molecule in the brain. Intrathecal administration provides several advantages to administration directly to the brain or ICV administration. Primarily, intrathecal administration allows one to avoid placement of a catheter or cannula through parenchymal tissue of the brain to reach a desired location or the cerebral ventricle. Accordingly, the subject to which the molecule is delivered is spared a great deal of risk and discomfort with IT delivery relative to ICV delivery. Further, the time involved with surgical procedures for delivering a molecule intrathecally is significantly less than delivering the molecule intracerebroventricularly.

Any other known or developed implantable or external infusion device or port may be employed.

A brief summary of various aspects of methods described herein are presented below:

A $1^{st}$ aspect is a method for affecting epilepsy in a subject, the method comprising: administering a liquid formulation comprising an antiepileptic compound to an CSF-containing intrathecal space of the subject; and administering a liquid formulation comprising a multidrug resistance protein (MRP) inhibitor compound to an CSF-containing intrathecal space of the subject.

A 2$^{nd}$ aspect is a method of aspect 1, wherein the liquid formulation comprising the antiepileptic compound is the same as the liquid formulation comprising the MRP inhibitor compound.

A 3$^{rd}$ aspect is a method of any of aspects 1 or 2, wherein the liquid formulation comprising the antiepileptic compound is administered to the CSF-containing intrathecal space at the same time as the liquid formulation comprising the MRP inhibitor compound.

A 4$^{th}$ aspect is a method of any of aspects 1 to 3, wherein the liquid formulation is delivered via a catheter having a delivery region placed in the CSF-containing space.

A 5$^{th}$ aspect is a method of any of aspects 1 to 4, wherein the CSF-containing space is selected from the group consisting of lumbar intrathecal space, thoracic intrathecal space, and cervical intrathecal space.

A 6$^{th}$ aspect is a method of any of aspects 1 to 5, wherein the CSF-containing space is the cervical intrathecal space.

A 7$^{th}$ aspect is a method of any of aspects 1 to 6, wherein the CSF-containing space is adjacent the second cervical vertebrae.

A 8$^{th}$ aspect is a method of any of aspects 1 to 7, wherein the antiepileptic compound is selected from carbamazepine, clobazam, clonazepam, eslicarbazepine acetate, felbamate, gabapentin, lacosamide, lamotrigine, levetiracetam, oxcarbazepine, phenobarbital, phenytoin, pregabalin, primidone, rufinamide, stiripentol, tiagabine, topiramate, valproic acid, vigabatrin, and zonisamide.

A 9$^{th}$ aspect is a method of any of aspects 1 to 8, wherein the antiepileptic compound is valproic acid.

A 10$^{th}$ aspect is a method of any of aspects 1 to 9, wherein the multidrug resistance protein (MRP) inhibitor compound is selected from probenecid, pyrimethamine, reversan, ceefourin 1, MK 571, and combinations thereof.

A 11$^{th}$ aspect is a method of any of aspects 1 to 10, wherein the multidrug resistance protein (MRP) inhibitor compound is probenecid.

A 12$^{th}$ aspect is a method for affecting epilepsy in a subject, the method comprising: administering a liquid formulation comprising valproic acid to an CSF-containing intrathecal space of the subject; and administering a liquid formulation comprising a multidrug resistance protein (MRP) inhibitor compound to an CSF-containing intrathecal space of the subject.

A 13$^{th}$ aspect is a method of aspect 12, wherein the liquid formulation comprising the valproic acid is the same as the liquid formulation comprising the MRP inhibitor compound.

A 14$^{th}$ aspect is a method of aspect 12, wherein the liquid formulation comprising the valproic acid is administered to the CSF-containing intrathecal space at the same time as the liquid formulation comprising the MRP inhibitor compound.

A 15$^{th}$ aspect is a method of any of aspects 12 to 14, wherein the liquid formulation is delivered via a catheter having a delivery region placed in the CSF-containing intrathecal space.

A 16$^{th}$ aspect is a method of any of aspects 12 to 15, wherein the CSF-containing intrathecal space is selected from the group consisting of lumbar intrathecal space, thoracic intrathecal space, and cervical intrathecal space.

A 17$^{th}$ aspect is a method of any of aspects 12 to 16, wherein the CSF-containing intrathecal space is the cervical intrathecal space.

An 18$^{th}$ aspect is a method of any of aspects 12 to 17, wherein the CSF-containing intrathecal space is adjacent the second cervical vertebrae.

A 19$^{th}$ aspect is a method of any of aspects 12 to 18, wherein the multidrug resistance protein (MRP) inhibitor compound is selected from probenecid, pyrimethamine, reversan, ceefourin 1, MK 571, and combinations thereof.

A 20$^{th}$ aspect is a method of any of aspects 12 to 19, wherein the multidrug resistance protein (MRP) inhibitor compound is probenecid.

Thus, embodiments of the METHODS OF ADMINISTERING ANTI-EPILEPSY AGENTS AND TRANSPORT INHIBITORS TO AREAS OF BRAIN are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for affecting epilepsy in a subject, the method comprising:
    administering a liquid formulation comprising an antiepileptic compound to a cerebrospinal fluid (CSF)-containing intrathecal space of the subject; and
    administering a liquid formulation comprising a multidrug resistance protein (MRP) inhibitor compound to an CSF-containing intrathecal space of the subject.

2. The method according to claim 1, wherein the liquid formulation comprising the antiepileptic compound is the same as the liquid formulation comprising the MRP inhibitor compound.

3. The method according to claim 1, wherein the liquid formulation comprising the antiepileptic compound is administered to the CSF-containing intrathecal space at the same time as the liquid formulation comprising the MRP inhibitor compound.

4. A method according to claim 1, wherein the liquid formulation is delivered via a catheter having a delivery region placed in the CSF-containing space.

5. A method according to claim 1, wherein the CSF-containing space is selected from the group consisting of lumbar intrathecal space, thoracic intrathecal space, and cervical intrathecal space.

6. A method according to claim 5, wherein the CSF-containing space is the cervical intrathecal space.

7. The method according to claim 6, wherein the CSF-containing space is adjacent the second cervical vertebrae.

8. A method according to claim 1, wherein the antiepileptic compound is selected from carbamazepine, clobazam, clonazepam, eslicarbazepine acetate, felbamate, gabapentin, lacosamide, lamotrigine, levetiracetam, oxcarbazepine, phenobarbital, phenytoin, pregabalin, primidone, rufinamide, stiripentol, tiagabine, topiramate, valproic acid, vigabatrin, and zonisamide.

9. The method according to claim 1, wherein the antiepileptic compound is valproic acid.

10. The method according to claim 1, wherein the multidrug resistance protein (MRP) inhibitor compound is selected from probenecid, pyrimethamine, reversan, ceefourin 1, MK 571, and combinations thereof.

11. The method according to claim 1, wherein the multidrug resistance protein (MRP) inhibitor compound is probenecid.

12. (CurrentlyAmended) A method for affecting epilepsy in a subject, the method comprising:
    administering a liquid formulation comprising valproic acid to an CSF-containing intrathecal space of the subject; and
    administering a liquid formulation comprising a multidrug resistance protein (MRP) inhibitor compound to cerebrospinal fluid (CSF)-containing intrathecal space of the subject.

13. The method according to claim 12, wherein the liquid formulation comprising the valproic acid is the same as the liquid formulation comprising the MRP inhibitor compound.

14. The method according to claim 12, wherein the liquid formulation comprising the valproic acid is administered to the CSF-containing intrathecal space at the same time as the liquid formulation comprising the MRP inhibitor compound.

15. A method according to claim 12, wherein the liquid formulation is delivered via a catheter having a delivery region placed in the CSF-containing intrathecal space.

16. A method according to claim 12, wherein the CSF-containing intrathecal space is selected from the group consisting of lumbar intrathecal space, thoracic intrathecal space, and cervical intrathecal space.

17. A method according to claim 12, wherein the CSF-containing intrathecal space is the cervical intrathecal space.

18. The method according to claim 12, wherein the CSF-containing intrathecal space is adjacent the second cervical vertebrae.

19. The method according to claim 12, wherein the multidrug resistance protein (MRP) inhibitor compound is selected from probenecid, pyrimethamine, reversan, ceefourin 1, MK 571, and combinations thereof.

20. The method according to claim 12, wherein the multidrug resistance protein (MRP) inhibitor compound is probenecid.

* * * * *